United States Patent [19]

Turner et al.

[11] Patent Number: 5,525,577

[45] Date of Patent: Jun. 11, 1996

[54] SAFENING EFFECT OF COMBINATIONS OF GLYPHOSATE AND ACIFLUORFEN

[75] Inventors: James C. Turner, Fuquay Varina, N.C.; Scott W. Gibson, Chesterville, Mo.

[73] Assignee: BASF Corporation, Mount Olive, N.J.

[21] Appl. No.: 340,922

[22] Filed: Nov. 17, 1994

[51] Int. Cl.$^6$ .................................................. A01N 57/04
[52] U.S. Cl. ............................................ 504/127; 504/144
[58] Field of Search ................................... 504/127, 128

[56] References Cited

U.S. PATENT DOCUMENTS

| | | | |
|---|---|---|---|
| Re. 31,455 | 12/1983 | Bayer et al. | 564/435 |
| 3,799,758 | 3/1974 | Franz | 71/86 |
| 3,853,530 | 12/1974 | Franz | 71/86 |
| 3,977,860 | 8/1976 | Franz | 71/86 |
| 3,988,142 | 10/1976 | Franz | 71/86 |
| 4,159,901 | 7/1979 | Beestman et al. | 71/86 |
| 4,405,531 | 9/1983 | Franz | 544/110 |
| 4,439,224 | 3/1984 | Schulteis | 71/76 |
| 5,015,283 | 5/1991 | Miyazawa et al. | 71/76 |
| 5,118,338 | 6/1992 | Moller | 71/86 |
| 5,147,444 | 9/1992 | Decor et al. | 71/86 |
| 5,180,414 | 1/1993 | Darchy et al. | 504/206 |

FOREIGN PATENT DOCUMENTS

WO84/03607  9/1984  WIPO.

*Primary Examiner*—Allen J. Robinson
*Assistant Examiner*—Brian G. Bembenick

[57] ABSTRACT

A method minimizing herbicidal injury to agricultural plants and crops while controlling undesirable weeds associated with said agricultural plants comprises applying thereto an effective quantity of N-phosphonomethyl-glycine and 4-trifluoromethyl-4-nitrodiphenyl ether, particularly acifluorfen.

4 Claims, No Drawings

SAFENING EFFECT OF COMBINATIONS OF GLYPHOSATE AND ACIFLUORFEN

FIELD OF THE INVENTION

The present invention relates to an improved herbicidal combination and method, and more particularly, to a mixture of N-phosphonomethylglycines, particularly glyphosate, with diphenyl ethers such as 4-trifluoromethyl-4-nitrodiphenyl ethers, particularly acifluorfen, which exhibits improved selectivity. The invention also relates to a method of increasing the herbicidal selectivity of N-phosphonomethyl-glycines, by adding one or more 4-trifluoromethyl-4-nitrodiphenyl ether compounds, notably acifluorfen thereto.

BACKGROUND OF THE INVENTION

The N-phosphonomethyl-glycines, of which glyphosate is a member, have proven to be an extremely valuable herbicides. Their soluble salts have been incorporated into various formulations which are extremely effective in controlling various plants and weeds that are detrimental to the growth and development of various cash crops and agricultural plants. N-phosphonomethyl-glycine can thus kill or inhibit the growth, reproduction, or proliferation of various weeds, which left untreated, would destroy or diminish the growth of crops, fruit trees, and other valuable plants.

Franz, U.S. Pat. No. 3,799,758, relates to N-phosphonomethylglycine and its derivatives which are useful as herbicides. This reference provides guidance into the preparation of various compounds which comprise the N-phosphonomethylglycine family.

Two other Franz references, U.S. Pat. Nos. 3,977,860 and 4,405,531, respectively, relate to salts of N-phosphonomethylglycine and to herbicidal compositions utilizing the esters of N-phosphonomethylglycine. The '531 patent, in particular, discloses the use of isopropyl amine salt of N-phosphonomethylglycine. This product is available from Monsanto Company of St. Louis, Mo. under the trademark ROUNDUP®.

Other insights into the art may be gleaned from a review of Moller, U.S. Pat. No. 5,118,338 and Darchy et al., U.S. Pat. No. 5,180,414. These references also relate to herbicidal compositions containing one or more salts of N-phosphonomethylglycine.

Unfortunately, N-phosphonomethyl-glycine is not particularly selective in its application as a herbicide. In many instances, it can kill or reduce the incidence of the "good" plants and crops, along with the weeds and other undesirable vegetation. Soybeans in particular have shown themselves to be especially vulnerable to the toxicity of N-phosphonomethyl-glycine and its salts. Data exists which show that a major percentage of a soybean crop can be damaged or lost upon each application of this herbicide. In typical applications of about 0.5 to 1.0 lbs/acre of N-phosphonomethylglycine, as much as 25-50% of the soybean plants will exhibit some form of visible injury. In some applications, this figure can be as high as 80%.

There thus exists a need in the art to develop effective herbicidal formulations containing N-phosphonomethylglycines which show greater selectivity in removing or controlling weeds, while minimally affecting valuable agricultural crops.

Acifluorfen is another valuable herbicide which has demonstrated toxic efficacy against a wide array of weeds. Acifluorfen is derived from the family of certain diphenylethers. Various salts of acifluorfen are available from BASF Corporation under the trademark BLAZER®. More specifically, Bayer et al., U.S. Pat. No. 4,063,929 (U.S. Pat. No. RE 31,455) is directed to herbicidal 4-trifluoromethyl-4-nitrodiphenyl ethers and the numerous salts thereof, and is incorporated herein by reference. The '929 patent lists the preparation and uses of various diphenyl ethers in herbicidal applications.

Combinations of N-phosphonomethylglycines and acifluorfen derivatives are known in the art as herbicides. For example, WO 84/03607, assigned to the Chevron Research Company, describes a glyphosate-type herbicidal composition with a minor amount of an acifluorfen type herbicide. The compositions reportedly exhibit an increased speed of phytotoxic action when compared with glyphosates alone.

Borrod et al., U.S. Pat. No. 5,147,444, also relates to a combination of glyphosate and acifluorfen for use as a herbicide. The patentees describe advantages of the combination as including increased speed of action, and improved activity. In addition, EP A 284,419 is directed to herbicides containing both acifluorfen and glyphosate.

It is unfortunate that none of the cited references appear to address the issue of how to avoid destroying or damaging valuable cash crops and other desirable vegetation by the use of the combination of the N-phosphonomethyl-glycines with acifluorfen.

It has now been discovered that a certain quantity of either herbicide together in combination exhibits what as been described as a "safening" effect. This means that when N-phosphonomethyl-glycine and acifluorfen are applied to crops, and especially soybeans, the incidence of damage to the crops is greatly reduced, as compared with similar applications of just the highly toxic N-phosphonomethylglycine alone. At the same time, the combination remains efficacious in reducing or eliminating undesirable weeds and other vegetation which is destructive to the crops.

OBJECTS OF THE INVENTION

It is therefore an object of the present invention to describe a composition and method for destroying weeds using an effective combination of N-phosphonomethyl-glycines and 4-trifluoromethyl-4-nitrodiphenyl ethers, said composition and method at the same time minimizing damage to cash crops.

It is a further object of the invention to increase the "safening" effect of certain herbicidal compositions, especially compositions containing N-phosphonomethyl-glycines.

It is still another object of the invention to significantly reduce and control the incidence of various weeds, while at the same reducing visible injury and death to soybean plants and other crops by using a combination of one or more N-phosphonomethyl-glycines and one or more 4-trifluoromethyl-4-nitrodiphenyl ethers.

Another object of the invention is to decrease the toxicity of N-phosphonomethyl-glycines against valuable agricultural crops upon applications thereto.

Yet another object of the invention is to utilize acifluorfen and its related family of compounds to reduce the toxicity of N-phosphonomethyl-glycines against soybeans and other cash crops.

SUMMARY OF THE INVENTION

These and other objects of the invention are achieved by providing a method of controlling the toxicity of N-phosphonomethyl-glycine as a herbicide in agricultural applications, which comprises adding thereto an effective quantity of one or more diphenyl ethers, in particular 4-trifluorometyl-4-nitrodiphenyl ethers, and notably acifluorfen.

The herbicidal selectivity of N-phosphonomethyl-glycine can also be increased by adding thereto an effective quantity of acifluorfen or one of its salts, as well as one or more members of the diphenyl ether family of compounds from which acifluorfen is derived. At the same time, herbicidal injury to agricultural plants and crops can be minimized and undesirable weeds which attack, damage and destroy the agricultural plants can be destroyed and controlled by applying thereto an effective quantity of N-phosphonomethyl-glycine(s) and acifluorfen/diphenyl ether(s).

Also provided as part of the invention is a selective herbicidal composition, comprising one or more N-phosphonomethylglycines and acifluorfen or associated diphenyl ethers, in which the composition minimizes injury and death to agricultural plants and crops, yet is effective against weeds and other undesirable vegetation associated with these agricultural plants and crops.

DETAILED DESCRIPTION OF THE PREFERRED EMBODIMENTS

The N-phosphonomethyl-glycines useful as part of the invention, as well as methods for making same, are described in Franz, U.S. Pat. Nos. 3,799,758 and 3,977,860, the salient portions of which are incorporated herein by reference. Briefly, the structural formula for N-phosphonomethyl-glycine is as follows:

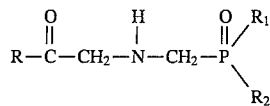

The various substituents comprising R, $R_1$ and $R_2$ are also found in the aforecited Franz references. In addition, the acid halides, amides, esters, and thioesters of N-phosphonomethyl-glycine, as well as the linear and cyclic anhydrides thereof, are useful in the invention. Those skilled in the art will also find that the various other derivatives and salts of the N-phosphonomethylglycines known in the art will be useful in the invention.

Particularly preferred for use in the composition and method of the invention is the compound glyphosate which is represented by the following formula:

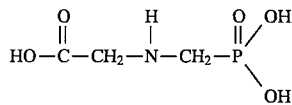

One source of glyphosate is the Monsanto Company of St. Louis, Mo. under the trademark ROUNDUP®.

Certain diphenyl ethers are also useful in the composition and method of the invention. The structural formula, and method of preparation for these compounds, and in particular 4-trifluorometyl-4-nitrodiphenyl ether compounds, more preferably acifluorfen, are further elaborated in Bayer et al., U.S. Pat. No. 4,063,929 (U.S. Pat. No. RE 31,455) heretofore set forth. 4-trifluoromethyl-4-nitrodiphenyl ether compounds can be represented by the following formula:

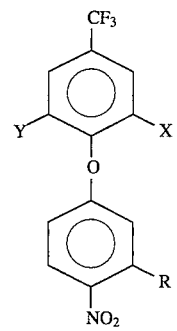

wherein R, X and Y are substituents as set forth in the U.S. Pat. No. RE 31,455 reference, as well as those known to persons skilled in the art.

Especially preferred are the compounds represented by the following formulas:

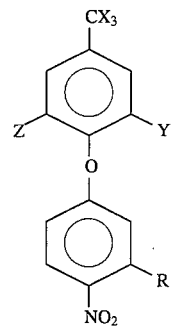

X, Y and Z = hydrogen, halogen
R = hydrogen, alkyl, halogen, cyano alkoxy, carboxy, carboalkoxy, carbamoyl, substituted alkoxycarbonyl, substituted carbomoyl and alkenyloxycarbonyl

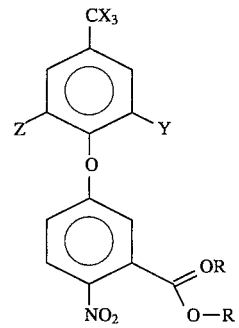

X, Y and Z = hydrogen, halogen
R = hydrogen, alkyl, halogen, cyano substituted amines, and substituted sulfonamides Acifluorfen is available from BASF Corporation of Mt. Olive, N.J. under the trademark BLAZER®. Acifluorfen may also be found in combination with another herbicide known as bentazon, known chemically as (3-(1-methylethyl)-1H-2,1,3-benzothiadiazin-4-(3H)-one 2,2-dioxide), and represented by the structural formula:

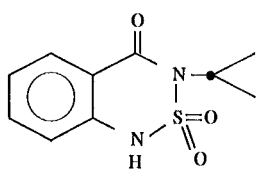

Two examples of an acifluorfen/bentazon combination are available from BASF Corporation under the trademarks GALAXY™ and STORM®. These acifluorfen/bentazon combinations may also be utilized with the aforementioned N-phosphonomethylglycine(s). At this time, however, it is somewhat more preferable to utilize acifluorfen alone.

N-phosphonomethylglycine(s), preferably glyphosate, and one or more diphenyl ethers, particularly 4-trifluorometyl-4-nitrodiphenyl ether compounds, preferably acifluorfen, are mixed together in a weight ratio within the range of about 8:1 to 1:1, and more preferably within the range of about 14:1 to 2:1. The actual weight quantities of the two herbicides which are ultimately utilized will depend upon the amount of land to which they will be applied. Typically, measurements are based upon pounds (lbs.) per acre. As an example, 0.5 pounds of glyphosate and 0.25 pounds of acifluorfen may be applied per acre; thus the two herbicides will be present in a weight ratio of about 2:1. The aforesaid amounts in pounds will double for two acres, and increase by a factor of ten for ten acres, and so on, while the relative weight ratio of about 2:1 will remain substantially constant.

The two preferred herbicide components heretofore set forth, N-phosphonomethylglycine and acifluorfen, may be further combined with one or more adjuvants to assist in their application to plants in the field. These adjuvants will aid the plants' uptake of the herbicides. They will also assist in a assuring a uniform application rate, and in the herbicide "sticking" to the undesirable weeds. There is a broad range of adjuvants available from various sources, including BASF Corporation, which are well known to the persons skilled in the art.

The skilled artisan will find that many adjuvants presently available will work well in the composition and method of the invention. Many of these adjuvants are surfactant or surfactant combinations. Some of these are available from BASF Corporation of Mt. Olive, N.J.

Urea ammonium nitrate is an especially useful adjuvant for use with N-phosphonomethylglycine and acifluorfen combination. It is often available as a 28% liquid formulation. Also useful is the product DASH® HC from BASF Corporation.

The adjuvants are typically added in a volumetric percentage. Urea ammonium nitrate will make up about 1.0–5.0% of the total volume of the herbicide composition, which will comprise herbicide plus adjuvant(s) plus water. The actual amount of adjuvant added is often based upon 20 gallons total of herbicide composition, which is the application rate per acre. At about 2.5%, which is preferred, and a total application area of one acre, the urea ammonium nitrate will comprise about 4 pints (2.5% of 20 gallons of herbicide composition). The DASH® HC adjuvant component will comprise about 0.1–1.0% of the total herbicide composition, and preferably about 0.4–0.7%. At about 0.63%, which is preferred, there will be about 1 pint of DASH® adjuvant utilized for every 20 gallons of herbicide composition. To this formulation, there will be added about 0.5 pounds of glyphosate (or other N-phosphonomethylglycine derivative) and about 0.25 pounds of acifluorfen in one embodiment. This formulation is then applied to crops and weeds in the manner and method known to those skilled in the art using known implements.

A typical herbicide formulation according to the invention will therefore comprise one or more N-phosphonomethylglycines, preferably glyphosate, and at least one diphenyl ether derivative, notably 4-trifluoromethyl-4-nitrodiphenyl ether and particularly acifluorfen, mixed together in a weight ratio within the range of about 8:1 to 1:1. That is, in one embodiment there will be a range of about 8 pounds of glyphosate for every approximate 1 pound of acifluorfen at one end of the spectrum, and about 1 pound of glyphosate for every 1 approximate pound of acifluorfen at the other end of the spectrum.

In a more preferred embodiment, there will be a ratio of N-phosphonomethylglycine(s) to diphenyl ether derivative(s) within the range of about 4:1 to 2:1. To any one of these mixtures will be added one or more adjuvants heretofore set forth in the volumetric percentages also set forth. Water will then make up the remainder of the herbicide composition so that there will be approximately 20 gallons of herbicide composition for every one acre of application. Those skilled in the art may of course discover that the amount of water and adjuvant(s) may be increased or decreased, depending upon the user's ultimate needs.

The compositions according to the various embodiments of the invention will find efficacy on a wide range of weeds and other vegetation. These will include foxtail, barnyardgrass, annual bluegrass, downy brome, blue mustard, tansy mustard, tumble mustard, wild mustard, umbrella spurry, barley, rye, field sandbur, shattercane, stinkgrass, wheat, morningglory, sicklepod, bulbous bluegrass, cheat, common chickweed, mousear chickweed, corn, jointed goatgrass, common groundsel, horseweed/marestail, common lambsquarters, field pennycress, fanweed, London rocket, Italian ryegrass, shepardspurse, annual spurge, buttercup, cocklebur, crabgrass, dwarf dandelion, smallseed falseflax, Carolina foxtail, seedling Johnsongrass, wild oats, fall panicum, Texas panicum, redroot pigweed, smooth pigweed, witchgrass, sicklepod, broadleaf signalgrass, red rice, teaweed, sprangletop, Carolina geranium, goosegrass, cutleaf evening primrose, Florida pulsey, sicklepod, Spanishneedles and filaree. This listing is by no means exhaustive and is provided by way of illustration only. It should not be construed as limiting the scope of the invention.

As heretofore noted, N-phosphonomethylglycines, and in particular glyphosate, have been shown to be particularly toxic against a significant number of valuable cash crops and plants, in addition to the weeds and other vegetation which they are designed to control. One of these crops is soybeans. Fairly substantial amounts of actual death or stand reduction, as well as visible injury to surviving soybean plants, has been shown when N-phosphonomethylglycines are applied alone, that is, without acifluorfen or a similar compound.

Upon application of the heretofore described herbicide compositions containing N-phosphonomethylglycine and acifluorfen, however, a significant reduction in both death or stand reduction and visible injury to surviving cash crops and plants has been noted. At the same time, the efficacy against weeds and other unwanted vegetation is maintained.

It is therefore within the scope of the invention to reduce actual cash crop plant loss by as much as about 20%, and preferably as much as about 40%, or even about 50% or more. In some embodiments, crop loss reduction may be as high as 75% when the herbicide compositions according to the various embodiments of the invention are utilized, as compared with N-phosphonomethylglycines alone.

Also significant is the fact that the herbicide compositions of the invention will reduce the incidence of visible damage and injury to surviving cash crops and plants, when compared with applications of N-phosphonomethylglycines alone. It is within the scope of the invention to reduce visible injury by as much as about 15%, and even 25% or more. In some embodiments, the reduction in visible injury may be as high as 40%, or even more.

EXAMPLES

The following examples are provided by way of illustrations only, and should not be construed as limiting the scope of the invention.

AMASS—smooth pigweed

Soybean death or strand reduction (AUDSUN) was 97% and 100% for Treatments 1 and 2, respectively, and was 40% for Treatment 6.

As Example 1 illustrates, treatment of glyphosate (ROUNDUP®) with bentazon (BASAGRAN®) was not nearly as effective as the treatment of glyphosate with acifluorfen (BLAZER®), both in terms of visible injury to the soybean plants, and the control of the weeds listed.

While the invention has been described in each of its various embodiments, it is expected that certain modifications thereto may be made by those skilled in the art without departing from its true spirit and scope as set forth in the specification and the accompanying claims.

| TREATMENT | RATE | (IOWA, MINNESOTA) % INJURY | | MINNESOTA % CONTROL | |
|---|---|---|---|---|---|
| | | (IOWA) VISIBLE INJURY | (MINN.) VISIBLE INJURY | SETFA EU 14-16 | SETLU EU 13-15 |
| 1. UNTREATED | | (15) | (18) | (8) | (1) |
| 2. ROUNDUP + DASH HC + 28% N | 0.5 + 0.63% + 2.5% | 15 | 25 | 85 | 35 |
| 3. ROUNDUP + DASH HC + 28% N | 1.0 + 0.63% + 2.5% | 80 | 60 | 99 | 99 |
| 4. ROUNDUP + BASAGRAN + DASH HC + 28% N | 0.5 + 0.5 + 0.63% + 2.5% | 25 | 25 | 85 | 40 |
| 5. ROUNDUP + BASAGRAN + DASH HC + 28% N | 0.5 + 0.75 + 0.63% + 2.5% | 25 | 40 | 40 | 20 |
| 6. ROUNDUP + BLAZER + DASH HC + 28% N | 0.5 + 0.25 + 0.63% + 2.5% | 7 | 12 | 99 | 99 |

| TREATMENT | RATE | MINNESOTA % CONTROL | | |
|---|---|---|---|---|
| | | ABUTH EU 14-16 | CHEAL EU 24-28 | AMASS EU 14-22 |
| 1. UNTREATED | | (7) | (20) | (10) |
| 2. ROUNDUP + DASH HC + 28% N | 0.5 + 0.63% + 2.5% | 60 | 35 | 90 |
| 3. ROUNDUP + DASH HC + 28% N | 1.0 + 0.63% + 2.5% | 65 | 70 | 93 |
| 4. ROUNDUP + BASAGRAN + DASH HC + 28% N | 0.5 + 0.5 + 0.63% + 2.5% | 98 | 55 | 80 |
| 5. ROUNDUP + BASAGRAN + DASH HC + 28% N | 0.5 + 0.75 + 0.63% + 2.5% | 97 | 45 | 85 |
| 6. ROUNDUP + BLAZER + DASH HC + 28% N | 0.5 + 0.25 + 0.63% + 2.5% | 85 | 60 | 98 |

BASAGRAN®—Bentazon—BASF Corp., Mt., Olive, N.J.
Rate of Application—20 gals./acre
ROUNDUP®, Blazer® and BASAGRAN® amounts in lbs.
DASH® HC amounts as percentage by volume
"N"—Urea Ammonium Nitrate (percentage by volume)
Iowa Visible Injury—47 days after Application (DAT)
  Weed Control not evaluated in Iowa due to flush(es) of weeds after application
Minn. Visible Injury and Weed Control—21 DAT
SETFA—giant foxtail
SETLU—geen foxtail
ABUTH—velvet leaf
CHEAL—lamb's quarters

What is claimed is:

1. A method for reducing the post emergence injury to soybean caused by ROUNDUP® by adding acifluorfen to said ROUNDUP® in a 2:1 ratio (ROUNDUP®:acifluorfen) and applying the composition to the soybean locus.

2. A method according to claim 1, wherein said composition comprises one or more adjuvants.

3. A method according to claim 2, wherein said adjuvant is urea ammonium nitrate.

4. A method according to claim 3, further comprising water.

* * * * *